(12) United States Patent
Yaron et al.

(10) Patent No.: US 7,290,880 B1
(45) Date of Patent: Nov. 6, 2007

(54) SYSTEM AND METHOD FOR PRODUCING A STEREOSCOPIC IMAGE OF AN EYE FUNDUS

(75) Inventors: Avi Yaron, Tenafly, NJ (US); Mark Schechterman, Nes-Ziona (IL)

(73) Assignee: Visionsense Ltd., Petah Tikva (IL)

( * ) Notice: Subject to any disclaimer, the term of this patent is extended or adjusted under 35 U.S.C. 154(b) by 0 days.

(21) Appl. No.: 11/493,200

(22) Filed: Jul. 26, 2006

(30) Foreign Application Priority Data

Jul. 27, 2005  (IL) ...................................... 169933

(51) Int. Cl.
  *A61B 3/14* (2006.01)
  *A61B 3/10* (2006.01)
  *A61B 3/02* (2006.01)
(52) U.S. Cl. ........................ 351/206; 351/205; 351/240
(58) Field of Classification Search ................ 351/205, 351/206, 240, 210, 211, 221
See application file for complete search history.

(56) References Cited

U.S. PATENT DOCUMENTS

| 5,355,253 A | 10/1994 | Nanjo et al. ................. 351/473 |
| 5,506,634 A | 4/1996 | Wei et al. .................... 351/221 |
| 6,726,326 B2 | 4/2004 | Fukuma et al. ............. 351/216 |

FOREIGN PATENT DOCUMENTS

JP  2006-087793  * 4/2006

* cited by examiner

*Primary Examiner*—Ricky Mack
*Assistant Examiner*—Jack Dinh
(74) *Attorney, Agent, or Firm*—Merchant & Gould P.C.

(57) ABSTRACT

A stereoscopic opthalmoscope for producing a stereoscopic image of an eye fundus, the stereoscopic opthalmoscope including a light source, for emitting a light beam, a light deflector, optically coupled with the light source, for deflecting the light beam into an eye, thereby illuminating the eye fundus of the eye, a relay lens, optically coupled with the eye, for receiving light beams reflected from the eye fundus, thereby producing a relayed three-dimensional image of the fundus, and a stereoscopic imaging apparatus, optically coupled with the relay lens, for stereoscopically acquiring the relayed three-dimensional image. The stereoscopic imaging apparatus includes a dual aperture element, a pixel array image detector and a lenticular lens layer, optically coupled with the pixel array image detector. The lenticular lens layer directs a right view scene of the relayed three dimensional image toward a first plurality of pixels of the pixel array image detector and a left view scene of the relayed three-dimensional image toward a second plurality of pixels of the pixel array image detector.

18 Claims, 9 Drawing Sheets

SYSTEM AND METHOD FOR PRODUCING A STEREOSCOPIC IMAGE OF AN EYE FUNDUS

FIELD OF THE DISCLOSED TECHNIQUE

The disclosed technique relates to optical devices for opthalmologic observation in general, and to a system for detecting a stereoscopic image pair of an eye fundus, in particular.

BACKGROUND OF THE DISCLOSED TECHNIQUE

The eye fundus is a medical term used to describe the structures at the posterior of a human eye (i.e., the interior lining of the eye), including the retina, optic disc (i.e., blind spot) and macula (i.e., fovea). Fundus observation devices, opthalmoscopes, and retinal cameras, are known in the art. Generally, a retinal observation device is placed at a predetermined distance in front of the examined eye. The observation device provides illumination to the retina through the eye pupil and forms a retinal image outside of the eye, by light reflected from the retina. An image detector detects this image, and a physician or an eye examiner may view this image using a display or an eyepiece.

Stereoscopic retinal cameras and opthalmoscopes are known in the art. Such cameras generally operate similarly to monocular retinal cameras, with the addition of a light guidance element (e.g., two-hole diaphragm) in order to split the light beam coming from the retina into two separate light beams (i.e., a right view and a left view). The split light beams traverse a path through two optical systems (i.e., a right view system and a left view system) toward two separate image detectors, which detect a right image and a left image of the retina. Alternatively, the right view and left view light beams traverse a path through the two optical systems toward a pair of eye-pieces, which are used by the physician for stereoscopic observation of the retina (e.g., each of the right and left view images are respectively provided to the right and left eyes of the physician).

Retinal cameras and opthalmoscopes can be utilized for biometric retinal imaging. Since the patterns of blood vessels on the retina are unique to each individual, this information can be used for the identification or identity verification of an individual (e.g., for allowing or denying access to certain areas or rooms in military compounds, power plants or other locations which are considered of high security classification, for allowing or denying performance of certain actions, such as cash retrieval from an ATM and the like). Retinal scanning devices are known in the art. Such devices scan the retina, analyze the patterns in the layer of blood vessels at the back of the eye and compare these patterns to files stored in a database, in order to identify or verify the identity of an individual.

U.S. Pat. No. 5,506,634 issued to Wei et al. and entitled "Fundus Illumination Apparatus Formed From Three, Separated Radiation Path System" is directed to an apparatus for illuminating a fundus of an eye using a beam of light. The apparatus includes an optical illumination path system and an optical observation path system. The optical illumination path system includes an incandescent light source, a first lens, a stop aperture, a first glass prism, a second lens, a third lens, a near-infrared filter and a second glass prism. The optical observation path system includes an ocular lens, a beam splitter, a first lens, a stop aperture, a second lens and a CCD camera. The observation path system is located directly in front of a photographed eye, and the illumination path system is located at a tilt angle with respect to the optical axis of the observation path system.

The light source emits light a beam, which passes through the first lens, the stop aperture, the first glass prism, the second lens, the third lens, the near-infrared filter and through the second glass prism. The light beam then impinges on the beam splitter, which directs it toward the ocular lens and into the eye. The light beam is reflected off of the fundus of the eye and passes through the ocular lens, the beam splitter, the first lens, the stop aperture and through the second lens, toward the CCD camera. The CCD camera is located on the focal plane of the combined assembly of the first lens, the stop aperture and the second lens, where an image of the fundus is obtained.

U.S. Pat. No. 5,355,253 issued to Nanjo et al. and entitled "Stereoscopic Retinal Camera" is directed to a system for photographing and observing an eye fundus in a stereoscopic manner. The system includes an illuminating optical section and a photographing optical section. The illuminating optical section includes a halogen lamp, a plurality of condenser lenses, a flash lamp, a beam splitter, a relay lens, a mirror, an aperture diaphragm and a perforated mirror.

The illuminating optical section is placed in a perpendicular manner to the optical axis of the photographing optical section, such that light beams emitted from the halogen lamp and the flash lamp are deflected toward of the eye. The aperture diaphragm has a circular slit, passing there through light beams emitted from the halogen lamp. The light beams are deflected by the mirror toward the optical axis of the photographing optical section. The condenser lens creates an image of the aperture diaphragm slit near the opening of the perforated mirror. The intermediate image of the slit is reflected by the perforated mirror, and the objective lens focuses the image of the slit near the eye cornea to illuminate the eye fundus.

The photographing optical section includes an objective lens, a two-hole diaphragm, a light splitting prism, two beam splitting prisms, two relay lenses, two focusing lenses, two image forming lenses and two films. The light splitting prism is a triangular shaped prism, located on the optical axis of the photographing optical section, such that the base of the triangle is perpendicular to the optical axis, facing the objective lens. The two-hole diaphragm is adjacent to the base of the triangular light splitting prism. The photographing optical section is placed in front of the eye, such that light beams reflected from the fundus are directed at the objective lens and the light splitting prism.

A light beam reflected from the fundus is focused by the objective lens, passes through the opening of the perforated mirror, through the two-hole diaphragm and into the light splitting prism. Light passing through the two-hole diaphragm is split into a right light beam and a left light beam. The light splitting prism interchanges the right light beam and the left light beam with each other, since the light beams originate in an inverted image of the fundus. The two beam splitting prisms collimate the right and left light beams, so that the collimated light beams pass along two parallel paths separated by a predetermined distance.

The separated light beams pass through the two relay lenses respectively, through the two focusing lenses and through the two image forming lenses. The image forming lenses form a right image and a left image of the fundus on the two films, respectively. The two focusing lenses are movable along the optical axis of the photographing optical system. The positions of the focusing lenses are adjusted according to the refracting power of the eye, to focus the image of the fundus on the each film. The two films then present images of the fundus, as viewed from two different viewpoints.

U.S. Pat. No. 6,726,326 B2 issued to Fukuma et al. and entitled "Observation Apparatus" is directed to an apparatus for observing an eye fundus, with an astigmatism canceling optical element. The apparatus includes an illumination optical system and an observation optical system. The illumination optical system includes a light source, a condenser lens, an illumination field stop, a collimator lens and a prism. The light source emits light toward the objective lens, which is also used by the observation optical system. The light passes through the condenser lens, the illumination field stop, the collimator lens and through the prism toward an eye fundus of an operating eye, so that the eye fundus is illuminated.

The observation optical system includes a right-eye observation optical system and a left-eye observation optical system. Each of the right-eye and the left-eye observation optical systems includes a zoom lens system, a beam splitter, an imaging lens, an image erecting prism, an interpupillary distance adjustment prism, a field stop, an eyepiece and an astigmatism canceling optical element. Each zoom lens system is composed of three lenses. Light reflected from the eye fundus is directed to the eyes of an apparatus operator through the objective lens and through the optical members of the right-eye and left-eye observation optical systems, so that the operator observes the eye fundus with both the right and left eyes.

A portion of the reflected light from the eye fundus is directed by a beam splitter toward an auxiliary observation optical system, for an assistant operator or toward an image pickup device, for producing an image of the eye fundus.

The astigmatism canceling optical element is utilized for canceling astigmatism power, caused when the optical members (i.e., lenses, mirrors and the like) are held against the cornea of the examined eye. The astigmatism canceling optical element includes a first and a second variable cylindrical lenses. The astigmatism canceling optical element is located between the zoom lens system and the imaging lens, in each of the right-eye and left-eye observation optical systems. The first variable cylindrical lens is composed of a convex cylindrical lens and the second variable cylindrical lens is composed of a concave cylindrical lens. The variable cylindrical lenses are located so as to be integrally rotatable about the observation optical axes, and to be rotatable relative to each other. When the variable cylindrical lenses are integrally rotated about the observation optical axes, the orientation of the astigmatism canceling optical element can be made to correspond to the orientation of the astigmatism caused according to how the optical members of the apparatus are held against the eye. In this manner, astigmatism canceling optical element is used to cancel the astigmatism of the examined eye.

SUMMARY OF THE DISCLOSED TECHNIQUE

It is an object of the disclosed technique to provide a novel method and system for producing a stereoscopic image of an eye fundus.

In accordance with the disclosed technique, there is thus provided a stereoscopic opthalmoscope for producing a stereoscopic image of an eye fundus. The stereoscopic opthalmoscope includes a light source, a light deflector, a relay lens and a stereoscopic imaging apparatus. The light source emits a light beam. The light deflector is optically coupled with the light source and deflects the light beam into an eye, thereby illuminating the eye fundus. The relay lens is optically coupled with the eye and receives light beams reflected from the fundus, thereby producing a relayed three-dimensional image of the fundus. The stereoscopic imaging apparatus is optically coupled with the relay lens and stereoscopically acquires the relayed three-dimensional image. The stereoscopic imaging apparatus includes a dual aperture element, a pixel array image detector and a lenticular lens layer. The lenticular lens layer is optically coupled with the pixel array image detector. The lenticular lens layer directs a right view scene of the relayed three-dimensional image toward a first plurality of pixels of the pixel array image detector, and a left view scene of the relayed three-dimensional image toward a second plurality of pixels of the pixel array image detector.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a dual aperture, single sensor stereoscopic camera, adapted for inspecting the inner parts of the human eye. This camera can detect stereoscopic image pairs of the eye fundus, and more specifically images of the retina (i.e., partial image of the fundus). Hereinafter, this camera will be referred to as a stereoscopic opthalmoscope.

Figure 1:
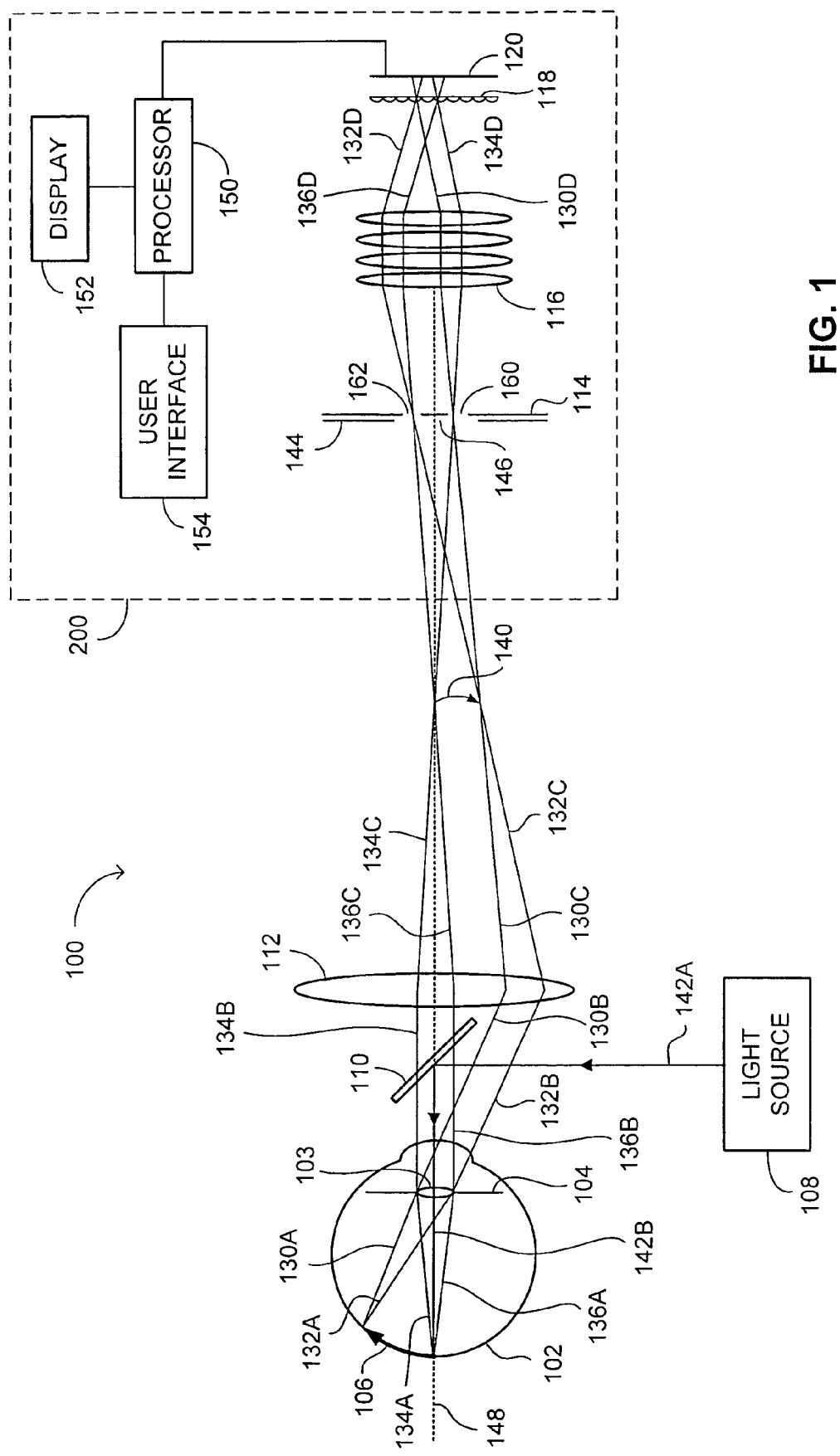
FIG. 1 is a schematic illustration of a stereoscopic opthalmoscope, constructed and operative in accordance with an embodiment of the disclosed technique.

Reference is now made to FIG. 1, which is a schematic illustration of a stereoscopic opthalmoscope, generally referenced 100, constructed and operative in accordance with an embodiment of the disclosed technique. Opthalmoscope 100 includes a light source 108, a light deflector 110, a relay lens 112 and a stereoscopic imaging apparatus 200. Stereoscopic imaging apparatus 200 includes a dual aperture element 114, an objective lens array 116, a lenticular lens layer 118, an image detector 120, a processor 150, a display 152 and a user interface 154. Image detector 120 is coupled with processor 150. Processor 150 is further coupled with display 152 and with user interface 154. Stereoscopic imaging apparatus 200 is described in further detail with connection to FIG. 2.

Dual aperture element 114 has two apertures 160 and 162 therein. Each of apertures 160 and 162 is in the form of a substantially round pinhole. An optical axis of apertures 160 and 162, of relay lens 112 and of objective lens array 116 is referenced 148. Apertures 160 and 162 are located substantially symmetrically about optical axis 148. Light source 108 and light deflector 110 constitute a fundus illumination section of opthalmoscope 100. Image detector 120 can be a charge-coupled device (CCD), complementary metal-oxide semiconductor (CMOS), and the like. User interface 154 can be a pointing device (e.g., a mouse, stylus and tablet), keyboard, and the like.

Opthalmoscope 100 detects a stereoscopic image pair of a retina 106 of an eye 102, using a single image detector. A user (i.e., a physician or an eye examiner, not shown) can view this stereoscopic image pair through display 152 or through a pair of eye-pieces (not shown). According to another aspect of the disclosed technique, the stereoscopic opthalmoscope can perform biometric retinal imaging (e.g., for identification or identity verification purposes). When the opthalmoscope performs biometric imaging, the processor is further coupled with a retinal image database. The processor compares the retina images obtained by the image detector with all the stored images or with certain stored images (i.e., as indicated by the individual, whose eye is being observed by the opthalmoscope), in order to identify the individual.

The device operator places opthalmoscope 100 in front of eye 102, such that optical axis 148 substantially aligns with the optical axis of an eye lens 103. In an alternative embodiment of the disclosed technique, the opthalmoscope can be placed automatically in front of the examined eye (e.g., by a robotic arm). Light deflector 110 is located between eye 102 and relay lens 112, on optical axis 148, such that light deflector 110 faces eye 102 and deflects light coming from light source 108 toward eye lens 103. It is noted that light deflector 110 can be located at various positions along optical axis 148. Light deflector 110 completely deflects light coming from light source 108 toward eye lens 103, and completely passes there through light coming from retina 106. Light source 108 can be for example a halogen lamp, an arc lamp, a light emitting diode (LED), an infrared lamp, a xenon lamp, and the like. Light source 108 illuminates retina 106 by emitting a light beam 142A substantially toward light deflector 110. Light deflector 110 directs light beam 142A as light beam 142B through eye lens 103, toward the inside of eye 102. It is noted that light source 108 may produce light at various wavelengths, depending on the desired image to be produced by opthalmoscope 100. It is further noted that alternatively, light source 108 may produce a plurality of light beams (not shown), which differ either spatially or chromatically.

Figure 3A:
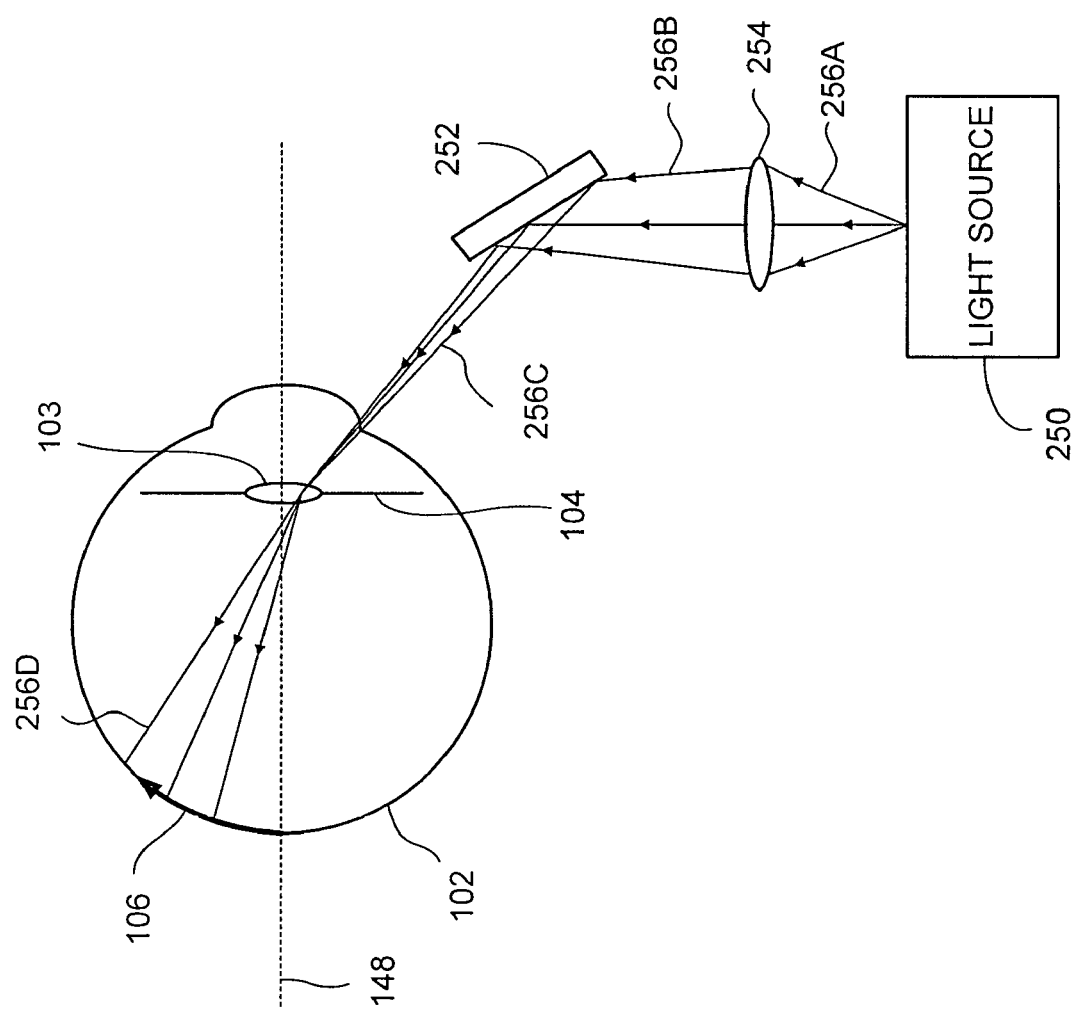
FIG. 3A is a schematic illustration of the fundus illumination section of the stereoscopic opthalmoscope of FIG. 1, constructed and operative according to another embodiment of the disclosed technique.

Reference is now made to FIG. 3A, which is a schematic illustration of a further embodiment of the fundus illumination section of opthalmoscope 100. According to this embodiment, the fundus illumination section includes a light source 250, a lens 254 and a light deflector 252. Light deflector 252 can be a folding prism or mirror. Light deflector 252 is placed remotely to optical axis 148 in proximity to eye 102, at a tilted angle relatively to optical axis 148. Lens 254 is placed between light deflector 252 and light source 250. Light source 250 emits light beams 256A, which are focused by lens 254, as light beams 256B toward light deflector 252. Light deflector 252 completely deflects light beams 256B as light beams 256C toward eye lens 103. Eye lens 103 directs light beams 256D toward the fundus of eye 102, thereby illuminating retina 106. Since light deflector 252 is remote to optical axis 148, light beams (not shown) which exit from retina 106 pass through eye lens 103, toward relay lens 112 (FIG. 1) without any deflection.

Figure 3B:
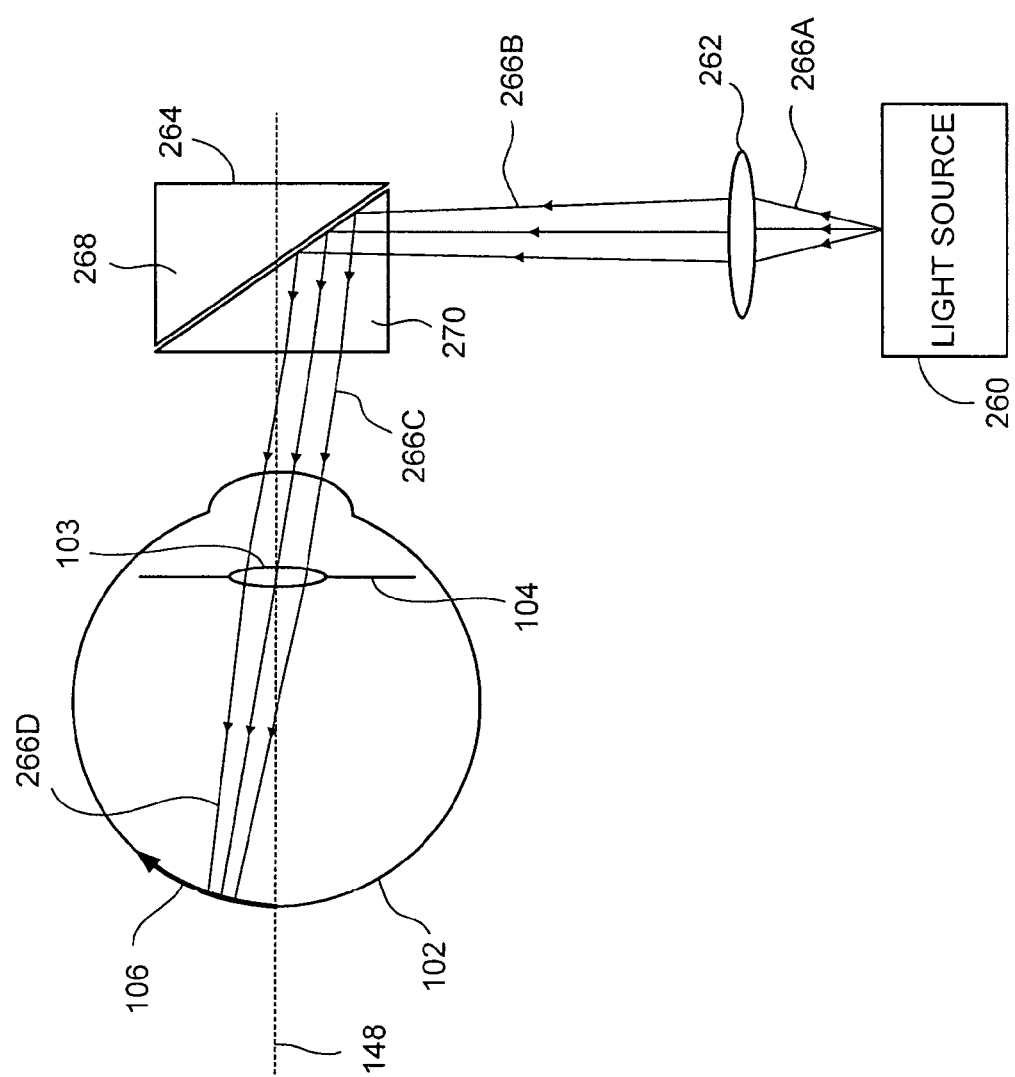
FIG. 3B is a schematic illustration of the fundus illumination section of the stereoscopic opthalmoscope of FIG. 1, constructed and operative according to a further embodiment of the disclosed technique.

Reference is now made to FIG. 3B, which is a schematic illustration of a further embodiment of the fundus illumination section of opthalmoscope 100. According to this embodiment, the fundus illumination section includes a light source 260, a lens 262 and a light deflector 264. Light deflector 264 is a two-prism total internal reflection (TIR) assembly, and includes a first prism 268 and a second prism 270. First prism 268 and second prism 270 are placed such that the two hypotenuses thereof face one another. Light deflector 264 is placed on optical axis 148 in proximity to eye 102. Lens 262 is placed between light deflector 264 and light source 260. Light source 260 emits light beams 266A, which are focused by lens 262, and directed as light beams 266B toward light deflector 264. Light beams 266B impinge on the hypotenuse of light deflector 264 at an angle (not shown) greater than the critical angle thereof. Thus, light deflector 264 completely deflects light beams 266B as light beams 266C toward eye lens 103. Eye lens 103 directs light beams 266C as light beams 266D toward the fundus of eye 102, thereby illuminating retina 106. Light beams (not shown) which exit from retina 106 and pass through eye lens 103, impinge on the hypotenuse of light deflector 264 at an angle smaller than the critical angle thereof, and therefore pass through light deflector 264 substantially without any deflection.

Reference is further made to FIG. 1. Relay lens 112 produces a relayed retina image 140 in a focal volume (not shown) between relay lens 112 and dual aperture element 114. Light beams 130A and 132A exit from a point in illuminated retina 106 toward an upper and a bottom point of eye lens 103, respectively. Eye lens 103 directs light beams 130B and 132B toward relay lens 112. Relay lens 112 directs light beams 130C and 132C toward apertures 160 and 162, respectively. Apertures 160 and 162 direct light beams 130C and 132C, respectively, toward objective lens array 116. Objective lens array 116 directs light beams 130D and 132D toward lenticular lens layer 118. Lenticular lens layer 118 directs light beams 130D and 132D toward certain cells (pixels) of image detector 120, respective of the direction from which light beams 130D and 132D arrive, such that a right image and a left image of relayed retina image 140 are created on image detector 120. Since retina 106 is a three dimensional object, relayed retina image 140 is a three dimensional image.

Similarly, light beams 134A and 136A exit from a point of retina 106, which is on optical axis 148, toward the upper and bottom points of eye lens 103, respectively. Eye lens 103 directs light beams 134B and 136B toward relay lens 112. Relay lens 112 directs light beams 134C and 136C toward apertures 160 and 162, respectively. Apertures 160 and 162 direct light beams 134C and 136C, respectively, toward objective lens array 116. Objective lens array 116 directs light beams 134D and 136D toward lenticular lens layer 118. Lenticular lens layer 118 directs light beams 134D and 136D toward certain cells of image detector 120, respective of the direction from which light beams 134D and 136D arrive.

Similarly, relay lens 112 produces a relayed pupil image 144 of an eye pupil 104 which coincides with dual aperture element 114, at a different location than relayed retina image 140. Relayed pupil image 144 has an imaged pupil aperture 146 therein, which encloses apertures 160 and 162.

In the described embodiment, the relay lens creates an image of the retina and an image of the pupil to a position outside the eye. Since the imaged pupil aperture encloses the apertures of the dual aperture element, the stereoscopic imaging apparatus is simulated to observe the retina, thereby allowing the opthalmoscope to generate a stereoscopic image pair thereof.

Figure 4A:
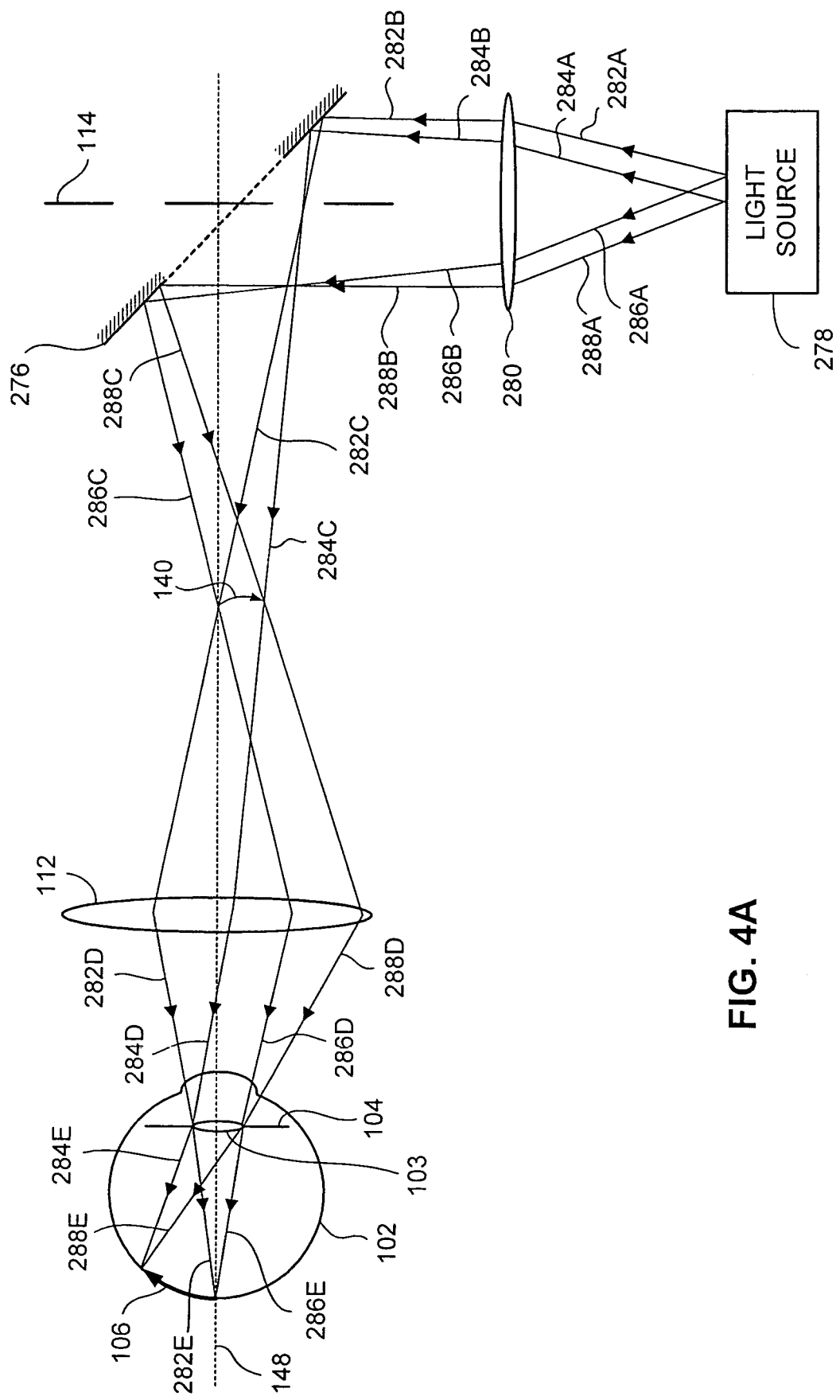
FIG. 4A is a schematic illustration of the fundus illumination section of the stereoscopic opthalmoscope of FIG. 1, constructed and operative according to another embodiment of the disclosed technique.
Figure 4B:
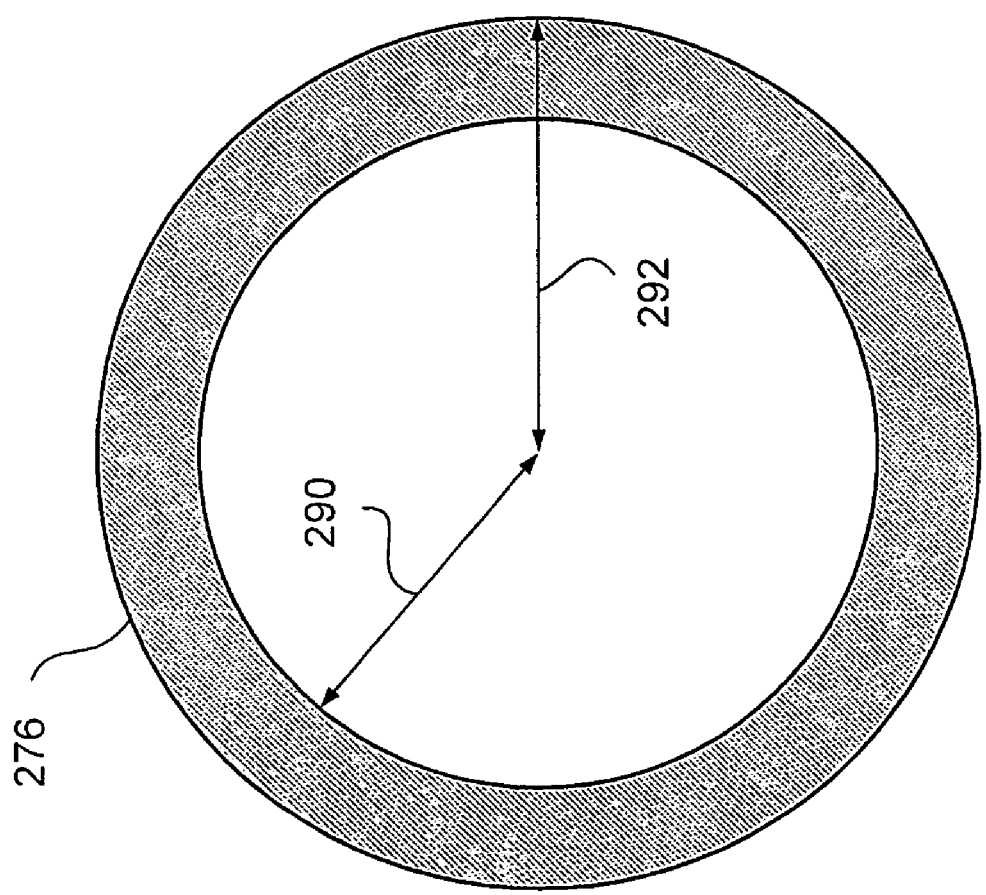
FIG. 4B is a front view of the annular mirror of FIG. 4A.

Reference is now made to FIGS. 4A and 4B. FIG. 4A is a schematic illustration of a further embodiment of the fundus illumination section of opthalmoscope 100. FIG. 4B is a front view of an annular mirror of FIG. 4A. According to the described embodiment, the fundus illumination section includes a light source 278, a lens 280 and an annular mirror 276. Annular mirror 276 has an inner radius 290 and an outer radius 292. Light source 278 is placed out of optical axis 148, in proximity to dual aperture element 114. Lens 280 is placed between optical axis 148 and light source 278. Annular mirror 276 is placed on optical axis 148, such that the center of dual aperture element 114 substantially coincides with the center of annular mirror 276, and dual aperture element 114 is enclosed within inner radius 290 of annular mirror 276 (i.e., annular mirror 276 surrounds dual aperture element 114). Annular mirror 276 is placed at a tilted angle relatively to light source 278 and to lens 280.

Light source 278 emits light beams 282A, 284A, 286A and 288A toward lens 280. Lens 280 directs light beams 282A, 284A, 286A and 288A as light beams 282B, 284B, 286B and 288B, respectively, toward annular mirror 276. Light beams 282B, 284B, 286B and 288B are reflected off of annular mirror 276 as light beams 282C, 284C, 286C and 288C, respectively, toward relay lens 112 (FIG. 1). Relay lens 112 directs light beams 282C, 284C, 286C and 288C as light beams 282D, 284D, 286D and 288D toward eye lens 103. Eye lens 103 directs light beams 282D, 284D, 286D and 288D as light beams 282E, 284E, 286E and 288E toward retina 106. In this manner light source 278 illuminates retina 106. Light beams (not shown) which exit retina 106, due to the illumination thereof, will traverse a path as described with reference to FIG. 1. After forming relayed retina image 140, these light beams may pass through inner radius 290 of annular mirror 276 toward dual aperture element 114 and objective lens array 116 (FIG. 1), without any deflection.

According to another embodiment of the disclosed technique, the fundus illumination section of opthalmoscope 100 may include an annular light source (not shown), which has an inner radius and an outer radius. The annular light source is placed around dual aperture element 114, such that both apertures thereof are enclosed within the inner radius of the annular light source. The annular light source emits a light beam (not shown) toward eye 102. The emitted light beam passes through eye lens 103, thereby illuminating retina 106. It is noted that the annular light source may be assembled from a plurality of light sources which, when placed in proximity to one another together, form the annular light source.

Reflected light beams (not shown) exit retina 106, due to the illumination thereof, will traverse a path as described with reference to FIG. 1. After forming relayed retina image 140, these reflected light beams may pass through the inner radius of the annular light source toward dual aperture element 114 and objective lens array 116 (FIG. 1), without any deflection.

Figure 2:
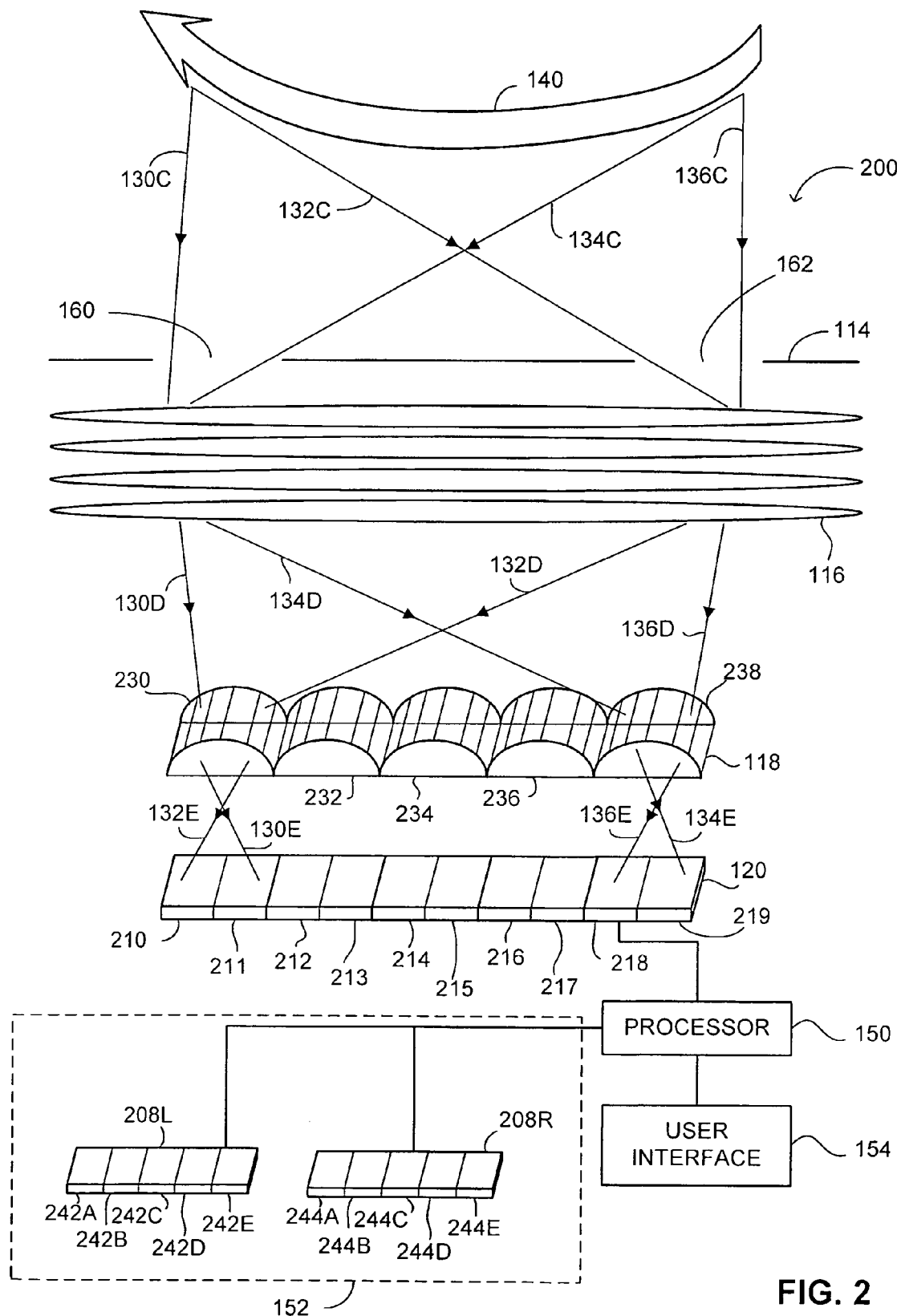
FIG. 2 is a schematic illustration of the stereoscopic imaging apparatus of FIG. 1, constructed and operative in accordance with another embodiment of the disclosed technique.

Reference is now made to FIG. 2, which is a schematic illustration of stereoscopic imaging apparatus 200 constructed and operative in accordance with an embodiment of the disclosed technique. Apparatus 200 includes a dual aperture element 114, an objective lens array 116, a lenticular lens layer 118, an image detector 120, a processor 150, a display 152 and a user interface 154. Display 152 includes two display units 208L and 208R. Image detector 120 is coupled with processor 150. Processor 150 is further coupled with display 152 and with user interface 154. A three-dimensional relayed retina image 140 is formed in front of apparatus 200 (e.g., as described with connection to FIG. 1).

Image detector 120 includes a plurality of sensors 210, 211, 212, 213, 214, 215, 216, 217, 218 and 219. Lenticular lens layer 118 includes a plurality of lenticular elements 230, 232, 234, 236 and 238. Each one of the lenticular elements is located above two light sensors, in a way that lenticular element 230 is located above sensors 210 and 211, lenticular element 232 is located above sensors 212 and 213, lenticular element 234 is located above sensors 214 and 215, lenticular element 236 is located above sensors 216 and 217 and lenticular element 238 is located above sensors 218 and 219.

Light sensors 210, 211, 212, 213, 214, 215, 216, 217, 218 and 219 detect light as directed by the lenticular lens elements 230, 232, 234, 236 and 238 and provide respective information to processor 150. Processor 150 processes this information, produces a pair of images, as will be explained in detail herein after, and provides them to display units 208R and 208L, which in turn produce visual representations of these images.

In general, each lenticular element directs light rays, which arrive from a predetermined direction, to a predetermined location and light rays which arrive from another predetermined direction, to another predetermined location. Hence, apparatus 200 utilizes lenticular lens layer 118 to distinguish between a right view image and a left view image, as described herein after.

Each of the display units 208R and 208L includes a plurality of display units also known as pixels. Display unit 208L includes pixels 242A, 242B, 242C, 242D and 242E. Display unit 208R includes pixels 244A, 244B, 244C, 244D and 244E. Using these pixels each of the display units produces an image, according to data provided from the processor. A user (i.e., a physician or an eye examiner, not shown) views the two images, each using a different eye, thereby acquiring a sensation of a three dimensional scene.

Light rays 134C and 136C represent a right-side image of retina image 140. Light rays 130C, and 132C represent a left side image of retina image 140. Light rays 132C and 136C pass through aperture 162, and light rays 130C and 134C pass through aperture 160, toward objective lens array 116. Objective lens array 116 directs light rays 130C, 132C, 134C and 136C so as to focus them on a plane determined by image detector 120, as light rays 130D, 132D, 134D and 136D, respectively. Hence, light rays 132D and 136D represent a focused left-side view of relayed retina image 140, and light rays and 130D and 134D represent a focused right-side view of relayed retina image 140.

Lenticular lens layer 118 directs focused left-side view light rays 132D and 136D to light sensors 210 and 218, respectively, as light rays 132E and 136E. In addition, lenticular lens layer 118 directs focused right side view light rays 130D and 134D to light sensors 211 and 219, respectively. In general, light sensors 211, 213, 215, 217 and 219 detect light rays which relate to a right-side of view image of relayed retina image 140 and light sensors were 210, 212, 214, 216, and 218, detect light rays which relate to a left-side view image of relayed retina image 140.

Hence, light sensors 210, 212, 214, 216 and 218 detect the left-side image of relayed retina image 140 while light sensors 211, 213, 215, 217 and 219 detects the right-side image of relayed retina image 140. Image detector 120 provides data relating to the detected light intensity at each of the light sensors to processor 150.

Processor 150 processes this data, produces a right side image from the data relating to the right-side image and a left-side image from the data relating to the left side and provides the respective image to respective display unit 208R and 208L.

In the present example, processor 150 utilizes the data received from sensors 210, 212, 214, 216 and 218 to determine the data provided to pixels 244A, 244B, 244C, 244D and 244E. Similarly, processor 150 utilizes the data received from sensors 211, 213, 215, 217 and 219 to determine the data which is to be provided to pixels 242A, 242B, 242C, 242D and 242E. According to the disclosed technique, the right-side image and the left-side image are detected at the same time and hence, can also be displayed at the same time.

According to another aspect of the disclosed technique, each of light sensors 210, 211, 212, 213, 214, 215, 216, 217, 218, and 219, include a plurality of color sensing elements, which together cover a predetermined spectrum. Processor 150 determines a shift between the right image and the left image for display 152 to display the images, wherein this shift is respective of vision characteristics of the user, thereby reducing vision associated discomfort while the user views the stereoscopic retinal images.

The user utilizes user interface 154 in order to perform various operations on the image displayed by display 152, or in order to alter physical parameters of opthalmoscope 100. For example, the user may change the distance between relay lens 112 and dual aperture element 114 (FIG. 1), to adjust the focus of the stereoscopic retina images, as displayed by display 152. In an alternative embodiment, opthalmoscope 100 may be operated automatically by processor 150. In this case, processor 150 can automatically alter the physical parameters of opthalmoscope 100, according to a predetermined set of rules (e.g., automatic focus adjustment, zoom adjustment, illumination properties).

According to another aspect of the disclosed technique, processor 150 performs image analysis of images obtained by opthalmoscope 100, during or after a treatment or an operation, and provide the user of opthalmoscope 100 (e.g., through display 152) with information regarding the progress of the treatment, the condition of the patient, and the like. For example, when a photodynamic therapy (PDT) treatment is performed on retina 106, a light-activated substance is injected into the bloodstream of the examinee and excited with illumination of suitable wavelength light, thereby selectively destroying undesirable blood vessels in retina 106. Another example is performing fluorescent angiography diagnosis of retina 106, by which a fluorescent dye is injected into the bloodstream of the examinee, and excited with illumination of suitable wavelength light. When such treatments are performed, opthalmoscope 100 can detect a video image of retina 106. Processor 150 analyzes the video images to determine the blood flow in the blood vessels in retina 106, and provides the user with this information during the treatment, in real time, thereby allowing improved treatment follow-up.

In case opthalmoscope 100 is used for medical examination of a patient, processor 150 may be further coupled with a database (not shown) of historical retinal images obtained at previous examinations. In this case, processor 150 analyzes the presently obtained images, so as to compare them with some of the historical images, thereby monitoring the medical situation of the patient (e.g., different stages of glaucoma, retinal blood vessels state in a diabetic patient, macula degeneration progress and the like).

Figure 5:
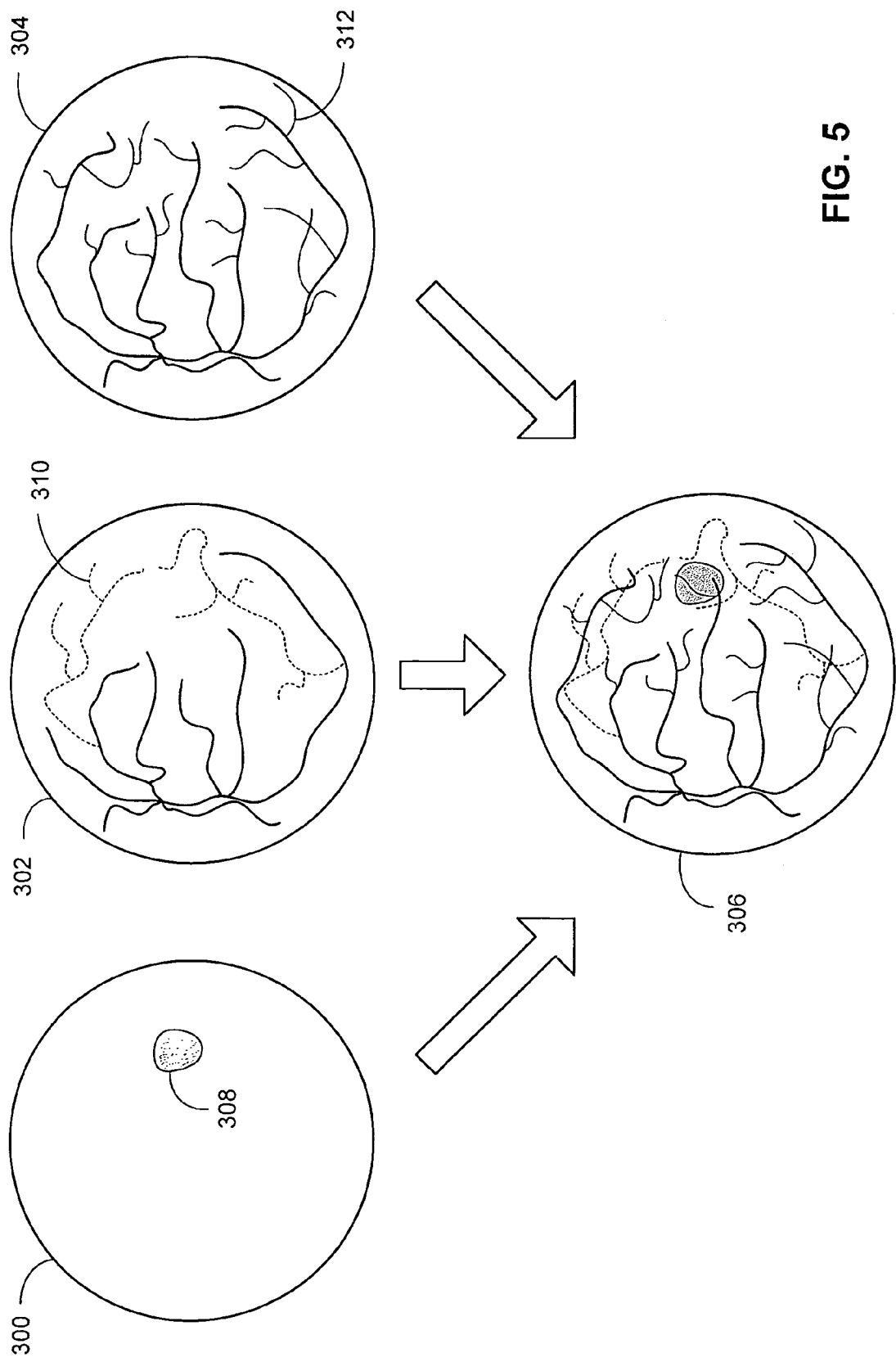
FIG. 5 is a schematic illustration of retinal images detected by the stereoscopic opthalmoscope of FIG. 1, a visible image, an infrared image, a photodynamic therapy (PDT) image and an overlay image.

According to another aspect of the disclosed technique, opthalmoscope 100 detects a plurality of retinal images, which differ in certain characteristics, and generates an overlay of the different retinal images. Reference is now made to FIG. 5, which schematically depicts various retinal images detected by opthalmoscope 100, a visible image 300, an infrared image 302, a fluorescent angiography image 304 and an overlay image 306. Each of retinal images 300, 302 and 304 provides a different view of the retina, and allows the examination of a different retinal feature.

Opthalmoscope 100 (FIG. 1) obtains visible image 300 by setting light source 108 to emit visible light (i.e., light at wavelengths of between about 400-700 nm). Light within this range of wavelengths is reflected from the retina surface, and detected by image detector 120. Thus, visible image 300 depicts a view of the retina surface and allows the user of opthalmoscope 100 to examine the retina surface.

Opthalmoscope 100 obtains infrared image 302 by setting light source 108 to emit infrared light (e.g., near-infrared at wavelengths of about 700 nm to 1200 nm). According to light-tissue interaction, infrared light penetrates the retina surface and is reflected from blood vessels lying deeper in the retina. The reflected light is detected by image detector 120. Thus, infrared image 300 depicts a view of blood vessel structure deeper in the retina and allows the opthalmoscope user to examine this deeper-lying structure.

Opthalmoscope 100 obtains fluorescent angiography image 304 after a fluorescent dye is injected to the bloodstream of the examinee, to observe the blood flow in the retina. Light source 108 emits light at wavelengths suitable for excitation of the fluorescent dye, which in turn emits light typically at near infrared wavelengths (e.g., about 850 nm). Alternatively, the fluorescent dye may emit light at visible wavelengths. The excitation light is then detected by image detector 120. Thus, fluorescent angiography image 304 depicts a view of the blood vessels in the retina, in which the fluorescent dye flows, and allows the opthalmoscope user to examine the vessel structure and blood flow and circulation in the retina.

Image detector 120 provides retinal images 300, 302 and 304, to processor 150. Processor 150 generates overlay image 306 by adding the light values at each pixel of the image detector in each of images 300, 302 and 304. Display 152 can show only overlay image 306, or each of images 300, 302 or 304 separately. Alternatively, display 152 can show overlay image 306 such that each of images 300, 302 and 304 are displayed in a different color or pattern. In this manner the user of opthalmoscope 100 can distinguish between information obtained from each of the overlaid images.

Certain features which are detectable in one of images 300, 302 and 304 may be undetectable in another of these images. For example, the fluorescent dye injected for obtaining fluorescent angiography image 304 flows in all the retinal blood vessels. Upon excitation, light is emitted even from very small retinal blood vessels 312. However, very small blood vessels 312 are undetectable in other images, such as in visible image 300 or in infrared image 302. Thus, fluorescent angiography image 304 provides additional information by showing the structure and blood flow in very small retinal blood vessels 312. Similarly, retina surface feature 308 is detectable in visible image 300, however undetectable in infrared image 302 or in fluorescent angiography image 304. In another example, deeper lying blood vessels 310 are detectable in infrared image 302, however undetectable in visible image 300 or in fluorescent angiography image 304. Overlaying images 300, 302 and 304 to single overlay image 306, yields an enriched visual presentation of the eye, which enhances features provided by each single image, thereby rendering retinal medical diagnosis and treatment more accurate.

Figure 6:
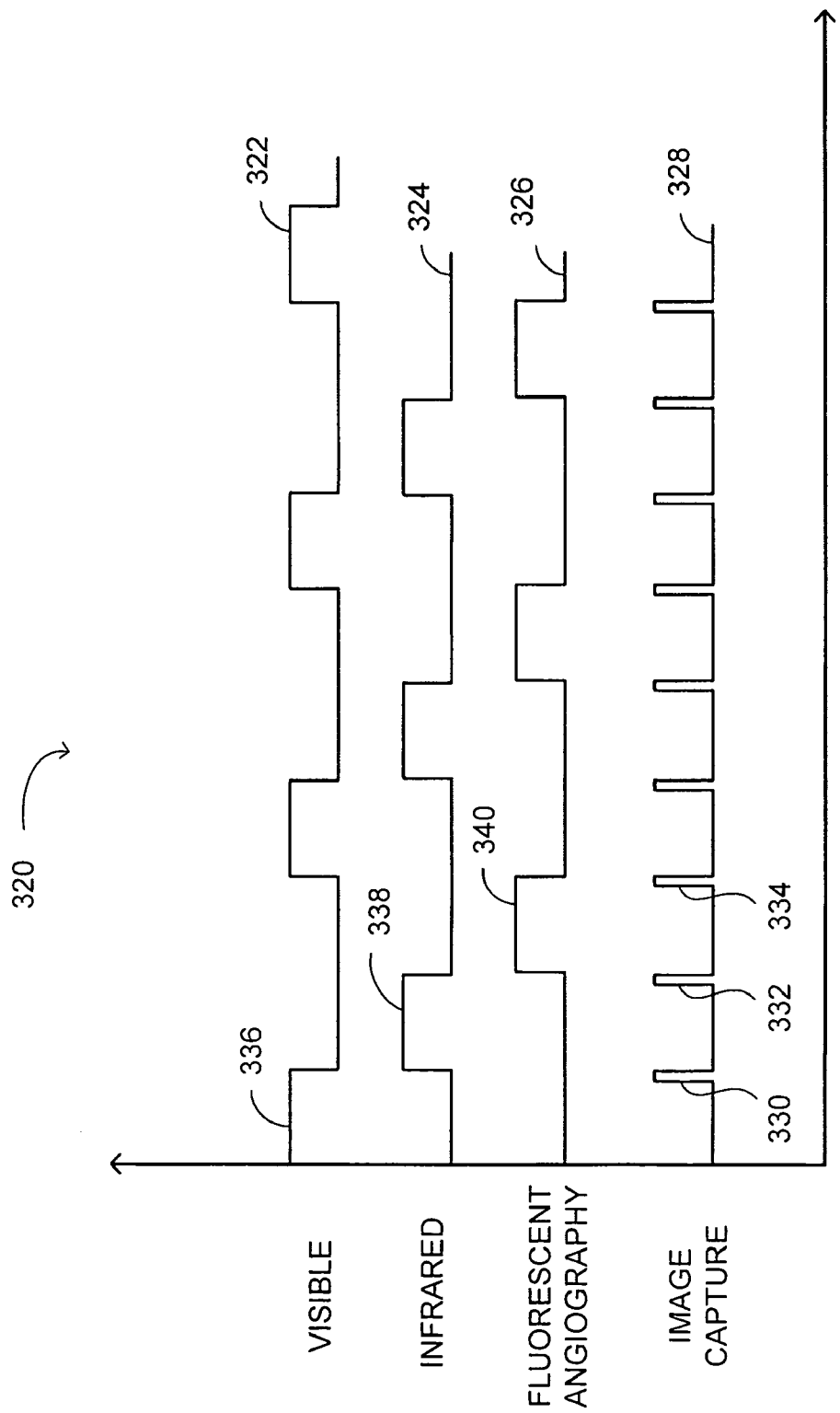
FIG. 6 is a schematic illustration of an illumination and image capture time scheme, for setting a scheme of operation for the stereoscopic opthalmoscope, according to the disclosed technique.

According to another aspect of the disclosed technique, opthalmoscope 100 is further operative to sequentially detect retinal images 300, 302 and 304, store them and then overlay them. In this case, light source 108 (FIG. 1) sequentially emits light at different wavelengths, according to a predetermined sequence. Reference is now made to FIG. 6, which is a schematic illustration of an illumination and image capture time scheme, generally referenced 320, according to another aspect of the disclosed technique. Time scheme 320 includes a visible illumination sequence 322, an infrared illumination sequence 324, a fluorescent angiography illumination sequence 326 and an image capture sequence 328.

Light source 108 emits visible light for a predetermined duration, according to visible illumination sequence 322. As a visible illumination pulse 336 ends, light source 108 emits infrared light, according to infrared illumination sequence 324. As an infrared illumination pulse 338 ends, light source 108 emits light suitable for the fluorescent dye excitation, according to fluorescent angiography illumination sequence 326 (i.e., a fluorescent angiography illumination pulse 340 commences).

Image detector 120 detects retinal images at times determined by image capture sequence 328. During visible illumination pulse 336, image detector 120 captures a visible retinal image (e.g. image 300 of FIG. 5), as directed by image capture pulse 330. During infrared illumination pulse 338, image detector 120 captures an infrared retinal image (e.g. image 302 of FIG. 5), as directed by image capture pulse 332. During fluorescent angiography illumination pulse 340, image detector 120 captures a fluorescent angiography retinal image (e.g. image 304 of FIG. 5), as directed by image capture pulse 334.

Illumination sequences 322, 324 and 326 include equal illumination periods, and equal cease periods for each illumination type. In an alternative embodiment, the illumination periods may vary for each illumination type. For example, visible illumination periods may be longer than infrared and fluorescent angiography periods, for certain examination or treatment needs. Shorter illumination and image capture periods may be used for movement detection, whereas longer illumination periods may be desirable in case illumination power is low. Illumination periods may be adjusted according to technical features of image detector 120, such as detector sensitivity. For example, if detector 120 has low sensitivity, the illumination periods should be prolonged, to enable detection of light by detector 120. Illumination time and power should be weighted, such that the total radiation illuminating the examined eye will not cause tissue damage to the examined eye. Thus illumination periods and power may be accordingly limited.

In the described embodiment, each period of time scheme 320 includes one visible illumination period, one infrared illumination period and one fluorescent angiography illumination period (i.e., time scheme 320 is: [visible-illumination→infrared-illumination→fluorescent-angiography-illumination]). Alternatively, time scheme 320 may include two illumination periods of a certain type instead of one. In this case, time scheme 320 may be, for example: [visible-illumination→infrared-illumination→visible-illumination→fluorescent-angiography-illumination]. Alternatively, time scheme 320 can be: [infrared-illumination→visible-illumination→infrared-illumination→fluorescent-angiography-illumination].

According to yet another aspect of the disclosed technique, opthalmoscope 100 can perform three-dimensional reconstruction of the retina, thereby generating a three-dimensional computerized model of the retina. Processor 150 can perform spatial measurements of retina 106. For example, measurement of distance between two points on retina 106, or measurement of a size of a certain feature (e.g., blood vessel or abnormality) on retina 106, as disclosed in U.S. provisional patent application No. 60/669,136, incorporated herewith by reference.

According to a further aspect of the disclosed technique, opthalmoscope 100 can produce still images of retina 106, as well as video images thereof, depending on the purpose for which opthalmoscope 100 is used. For example, still images are desirable for biometric identification or identity verification of an individual, whereas video images are desirable for medical examination and medical follow-up of a patient. Specifically, still images may be used for medical condition follow-up, and video images may be preferable for an ongoing treatment or operation, such as PDT treatment, or a fundus functional examination, such as fluorescent angiography.

Figure 7:
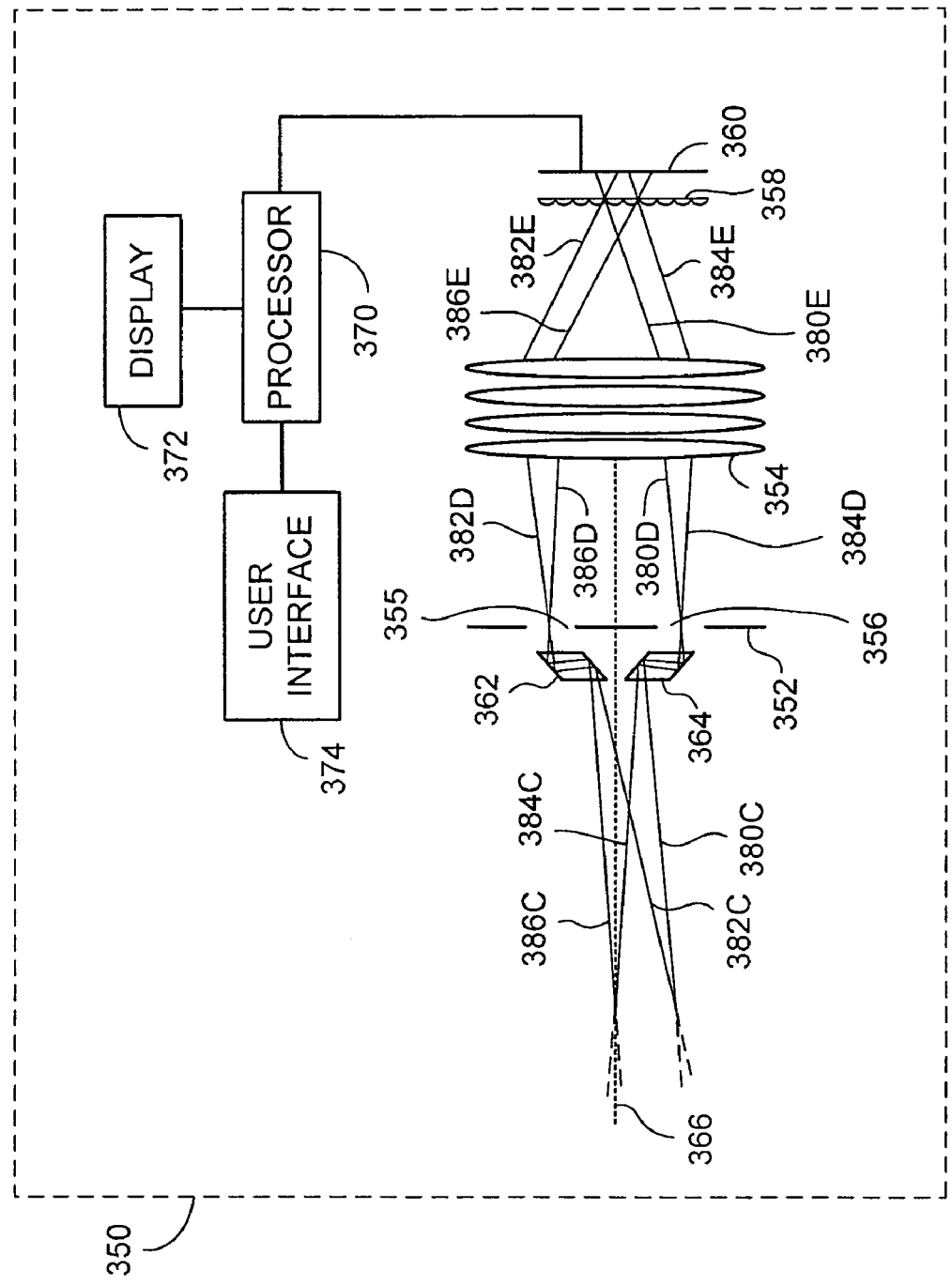
FIG. 7 is a schematic illustration of the stereoscopic imaging apparatus of FIG. 1, constructed and operative in accordance with a further embodiment of the disclosed technique.

Reference is now made to FIG. 7, which is a schematic illustration of a stereoscopic imaging apparatus, generally referenced 350, constructed and operative in accordance with a further embodiment of the disclosed technique. According to the described embodiment, stereoscopic imaging apparatus 350 can replace stereoscopic imaging apparatus 200 in opthalmoscope 100, with reference to FIG. 1 and FIG. 2. In the described embodiment the stereoscopic image resolution and image quality can be improved, by virtually increasing the interpupillary distance in stereoscopic imaging apparatus 200.

Stereoscopic imaging apparatus 350 includes a first parallelogramic prism 362, a second parallelogramic prism 364, a dual aperture element 352, an objective lens array 354, a lenticular lens layer 358, an image detector 360, a processor 370, a display 372 and a user interface 374. Image detector 360 is coupled with processor 370. Processor 370 is further coupled with display 372 and with user interface 374.

Dual aperture element 352 has a first aperture 355 and a second aperture 356 therein. Each of apertures 355 and 356 is in the form of a substantially round pinhole. An optical axis of apertures 355 and 356 and of objective lens array 354 is referenced 366. Apertures 355 and 356 are located substantially symmetrically about optical axis 366. Image detector 360 can be a charge-coupled device (CCD), complementary metal-oxide semiconductor (CMOS), and the like. User interface 374 can be a pointing device (e.g., a mouse, stylus and tablet), keyboard, and the like. First parallelogramic prism 362 and second parallelogramic prism 364 are placed in proximity to dual aperture element 352, in proximity to apertures 355 and 356, respectively, and are substantially symmetrical about axis 366. Parallelogramic prisms 362 and 364 are placed in an opposite manner (i.e., they are rotated at an angle of 180° relative to one another). Objective lens array 354 is placed between dual aperture element 352 and lenticular lens layer 358. Image detector 360 is placed on the other side of lenticular lens layer 358.

Light beams 380C, 382C, 384C and 386C are generated in a similar manner to light beams 130C, 132C, 134C and 136C with connection to FIG. 1, respectively. Light beams 380C, 382C, 384C and 386C originate in an eye retina (not shown), and intersect such that they create a three-dimensional relayed retina image (not shown), similarly to relayed retina image 140 of FIG. 1.

When a light beam enters a parallelogramic prism, such as parallelogramic prisms 362 and 364, it is reflected from the inner walls thereof, and exits the prism in a substantially similar direction to the direction of entry, only with a certain shift. In this manner, when light beams 382C and 386C enter first parallelogramic prism 362, they are shifted further away from axis 366. First parallelogramic prism 362 directs light beams 382C and 386C as light beams 382D and 386D, respectively. Similarly, when light beams 380C and 384C enter second parallelogramic prism 364, they are shifted further away from axis 366. Second parallelogramic prism 364 directs light beams 380C and 384C as light beams 380D and 384D, respectively.

Light rays 382D and 386D pass through first aperture 355, and light rays 380D and 384D pass through second aperture 356, toward objective lens array 354. Objective lens array 354 directs light rays 380D, 382D, 384D and 386D so as to focus them on a plane determined by image detector 360, as light rays 380E, 382E, 384E and 386E, respectively. Hence, light rays 382E and 386E represent a focused left-side view of the relayed retina image, and light rays 380E and 384E represent a focused right-side view of the relayed retina image.

In this manner, light beams 380D, 382D, 384D and 386D pass through apertures 355 and 356 at a greater distance, than they would if no parallelogramic prisms were present. Thus, the effective distance between apertures 355 and 356 is increased. Increasing of this distance also increases the stereoscopic image resolution and image quality, provided by stereoscopic imaging apparatus 350.

It is noted that the operation of lenticular lens layer 358, image detector 360, processor 370, display 372 and user interface 374 is similar to the operation of these elements of stereoscopic imaging apparatus 200, as described with connection to FIG. 1 and FIG. 2.

It will be appreciated by persons skilled in the art that the disclosed technique is not limited to what has been particularly shown and described hereinabove. Rather the scope of the disclosed technique is defined only by the claims, which follow.

The invention claimed is:

1. Stereoscopic opthalmoscope for producing a stereoscopic image of an eye fundus, the stereoscopic opthalmoscope comprising:
    a light source, for emitting a light beam;
    a light deflector, optically coupled with said light source, for deflecting said light beam into an eye, thereby illuminating the eye fundus of said eye;
    a relay lens, optically coupled with said eye, for receiving light beams reflected from said eye fundus, thereby producing a relayed three-dimensional image of said fundus; and
    a stereoscopic imaging apparatus, optically coupled with said relay lens, for stereoscopically acquiring said relayed three-dimensional image, said stereoscopic imaging apparatus including a dual aperture element, a pixel array image detector and a lenticular lens layer, optically coupled with said pixel array image detector, said lenticular lens layer directing a right view scene of said relayed three-dimensional image toward a first plurality of pixels of said pixel array image detector and a left view scene of said relayed three-dimensional image toward a second plurality of pixels of said pixel array image detector.

2. The stereoscopic opthalmoscope according to claim 1, wherein said stereoscopic imaging apparatus further includes an objective lens array, said objective lens array optically coupled with said dual aperture element, for directing light beams passing through the apertures of said dual aperture element, toward said lenticular lens layer.

3. The stereoscopic opthalmoscope according to claim 1, wherein said stereoscopic imaging apparatus further includes:
    a processor, coupled with said pixel array image detector, for processing information received from said pixel array image detector, said processor separating said information from said first plurality of pixels respective of said right view scene, and from said second plurality of pixels respective of said left view scene, thereby producing a right view image of said eye fundus and a left view image of said eye fundus; and
    a display, coupled with said processor, for producing visual representations of said right view image and of said left view image, according to data provided by said processor.

4. The stereoscopic opthalmoscope according to claim 3, wherein said stereoscopic imaging apparatus further includes a user interface, coupled with said processor, for allowing a user of said stereoscopic opthalmoscope to alter physical properties of said stereoscopic opthalmoscope.

5. The stereoscopic opthalmoscope according to claim 3, wherein said stereoscopic imaging apparatus further includes a user interface, coupled with said processor, for modifying image processing parameters.

6. The stereoscopic opthalmoscope according to claim 3, further comprising a storage unit, coupled with said processor, for storing images captured by said pixel array image detector.

7. The stereoscopic opthalmoscope according to claim 3, wherein said processor generates an overlay image from a plurality of images, each of said images produced by detecting light at different ranges of wavelengths.

8. The stereoscopic opthalmoscope according to claim 1, further comprising an illumination objective lens, optically coupled with said light source, for focusing said light beam onto the surface of said light deflector.

9. The stereoscopic opthalmoscope according to claim 8, wherein said light deflector is selected from the list consisting of:
    a mirror;
    a folding prism; and
    a two-prism total internal reflection (TIR) assembly, said two-prism TIR assembly including a first prism and a second prism, said first prism and said second prism are placed, such that the two hypotenuses of said first prism and of said second prism, face one another.

10. The stereoscopic opthalmoscope according to claim 8, wherein said light deflector includes an annular mirror, said annular mirror having an inner radius and an outer radius, wherein said inner radius encloses the apertures of said dual aperture element.

11. The stereoscopic opthalmoscope according to claim 1, wherein said light source emits a visible light beam, having a wavelength of between about 400 nm and 700 nm.

12. The stereoscopic opthalmoscope according to claim 1, wherein said light source emits an infrared light beam, having a wavelength of between about 700 nm and 3,000 nm.

13. The stereoscopic opthalmoscope according to claim 1, wherein said light source emits a light beam at a wavelength suitable for the excitation of a light-activated substance, said light-activated substance being present in the blood vessels of said eye fundus, thereby inducing selective destruction of said blood vessels in said eye fundus.

14. The stereoscopic opthalmoscope according to claim 13, wherein said light beam is a visible light beam.

15. The stereoscopic opthalmoscope according to claim 13, wherein said light beam is an infrared light beam.

16. The stereoscopic opthalmoscope according to claim 1, wherein said light source emits a light beam at a wavelength suitable for the excitation of a fluorescent dye, said fluorescent dye being present in the blood vessels of said eye fundus, thereby inducing said fluorescent dye to emit excitation light.

17. The stereoscopic opthalmoscope according to claim 1, wherein said light source sequentially emits alternating light beams of different ranges of wavelengths, according to an illumination time scheme, said illumination time scheme determining the time and duration of each of said alternating light beams.

18. The stereoscopic opthalmoscope according to claim 1, wherein said stereoscopic imaging apparatus further includes a first parallelogramic prism, optically coupled with a first aperture of said dual aperture element, and a second parallelogramic prism, optically coupled with a second aperture of said dual aperture element, for shifting the light beams entering said first parallelogramic prism and said second parallelogramic prism further away from one another, thereby allowing the use of increased distance between said first aperture and said second aperture.

* * * * *